US00PP27366P2

(12) United States Plant Patent
Horner

(10) Patent No.: US PP27,366 P2
(45) Date of Patent: Nov. 15, 2016

(54) SHRUB ROSE PLANT NAMED 'HORNIMROD'

(50) Latin Name: *Rosa hybrida*
Varietal Denomination: Hornimrod

(71) Applicant: Heather Horner, Stansted, Essex (GB)

(72) Inventor: Colin Horner, Stansted (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/998,234

(22) Filed: Oct. 11, 2013

(51) Int. Cl.
*A01H 5/02* (2006.01)

(52) U.S. Cl.
USPC ..... Plt./107

(58) Field of Classification Search
USPC ..... Plt./107
See application file for complete search history.

(56) References Cited

PUBLICATIONS

UPOV Record Detail 'Hornimrod' (retrieved from UPOV search Mar. 26, 2015).*

* cited by examiner

*Primary Examiner* — Keith Robinson
(74) *Attorney, Agent, or Firm* — C. A. Whealy

(57) ABSTRACT

A new and distinct cultivar of Rose plant named 'Hornimrod', characterized by its upright and mounding plant habit; glossy green-colored leaves; freely branching growth habit; freely flowering habit; large hot pink-colored flowers; resistance to Black Spot; and good garden performance.

2 Drawing Sheets

Botanical designation: *Rosa hybrida.*
Cultivar denomination: 'HORNIMROD'.

BACKGROUND OF THE INVENTION

The present Invention relates to a new and distinct Rose plant, botanically known as *Rosa hybrida*, commercially used as an ornamental Shrub Rose and hereinafter referred to by the name 'Hornimrod'.

The new Rose plant is a product of a planned breeding program conducted by the Inventor in Stausted, Essex, United Kingdom. The objective of the breeding program was to develop new uniform and disease-resistant shrub Rose plants with large and attractive flowers.

The new Rose plant originated from a cross-pollination made by the Inventor in 1998 of *Rosa sempervirens* 'Meidomonac', disclosed in U.S. Plant Pat. No. 5,105, as the female, or seed, parent with an unnamed proprietary seedling selection of *Rosa hybrida*, not patented, as the male, or pollen, parent. The new Rose plant was discovered and selected by the Inventor in 2004 as a single flowering plant within the progeny of the stated cross-pollination in a controlled environment in Stausted, Essex, United Kingdom.

Asexual reproduction of the new Rose plant by softwood cuttings at Stausted, Essex, United Kingdom since 2004, has shown that the unique features of this new Rose plant are stable and reproduced true to type in successive generations of asexual reproduction.

SUMMARY OF THE INVENTION

The following traits have been repeatedly observed and are determined to be the unique characteristics of 'Hornimrod'. These characteristics in combination distinguish 'Hornimrod' as a new and distinct Rose plant:

1. Upright and mounding plant habit.
2. Glossy green-colored leaves.
3. Freely branching growth habit.
4. Freely flowering habit.
5. Large hot pink-colored flowers.
6. Resistant to Black Spot (*Diplocarpon rosae*).
7. Good garden performance.

Plants of the new Rose differ from plants of the female parent, 'Meidomonac', in the following characteristics:

1. Plants of the new Rose are more upright than plants of 'Meidomonac'.
2. Flowers of plants of the new Rose have fewer petals than flowers of plants of 'Meidomonac'.
3. Plants of the new Rose and 'Meidomonac' differ in flower color as plants of 'Meidomonac' have clear pink-colored flowers.
4. Plants of the new Rose are more resistant to Black Spot than plants of 'Meidomonac'.

Plants of the new Rose differ from plants of the male parent selection in the following characteristics:

1. Plants of the new Rose are more freely flowering than plants of the male parent selection.
2. Flowers of plants of the new Rose not as fragrant as flowers of plants of the male parent selection.
3. Plants of the new Rose and the male parent selection differ in flower color as plants of the male parent selection have apricot-colored flowers.
4. Plants of the new Rose are more resistant to Black Spot than plants of the male parent selection.

Plants of the new Rose can be compared to plants of the *Rosa hybrida* 'Chewallbell', disclosed in U.S. Plant Pat. No. 26,817. Plants of the new Rose differ from plants of 'Chewallbell' in the following characteristics:

1. Plants of the new Rose are more upright than plants of 'Chewallbell'.
2. Flowers of plants of the new Rose are not as flat as flowers of plants of 'Chewallbell'.
3. Plants of the new Rose and 'Chewallbell' differ in flower color as plants of 'Chewallbell' have clear salmon pink-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'Hornimrod' grown in a container.

The photograph on the second sheet is a close-up view of a typical flowering plant of 'Hornimrod'.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown in 1.5-gallon containers during the summer in an outdoor nursery in Grand Haven, Mich. and under cultural practices typical of commercial Rose production. Plants were 1.5 years old when the photographs and description were taken. In the following description, color references are made to The Royal Horticultural Society Colour Chart, 1995 Edition, except where general terms of ordinary dictionary significance are used.

Botanical classification: *Rosa hybrida* 'Hornimrod'.

Parentage:

*Female, or seed, parent.*—*Rosa sempervirens* 'Meidomonac', disclosed in U.S. Plant Pat. No. 5,105.

*Male, or pollen, parent.*—Unnamed proprietary seedling selection of *Rosa hybrida*, not patented.

Propagation:

*Type.*—By softwood cuttings.

*Time to initiate roots.*—About 12 days at 25° C.

*Time to produce a rooted young plant.*—About three months at 25° C.

*Root description.*—Somewhat fibrous, fine to thick; white, close to 155A, to brown, close to 200B in color.

*Rooting habit.*—Freely branching; dense.

Plant description:

*Plant form.*—Upright and mounding perennial Shrub Rose.

*Growth habit.*—Vigorous growth habit; rapid growth rate.

*Branching habit.*—Freely branching habit; about twelve primary lateral branches develop per plant; dense and bushy growth habit; pinching enhances lateral branch development.

*Plant height.*—About 30 cm.

*Plant width (spread).*—About 47 cm.

*Lateral branches.*—Length: About 26 cm. Diameter: About 4 mm. Internode length: About 2 cm. Strength: Strong. Texture: Smooth, glabrous. Color: Close to 144A. Thorns: Density: About three to four thorns per node on a developed lateral branch. Shape: Triangular with sharp acuminate apices. Height: About 5 mm. Diameter, at base: About 5 mm. Color, immature: Close to 153B; towards the apex, close to 178B. Color, mature: Close to 165A.

Leaf description:

*Arrangement.*—Alternate; pinnately compound with about three to five leaflets per leaf.

*Leaflet length.*—About 4 cm.

*Leaflet width.*—About 2.3 cm.

*Leaflet shape.*—Ovate.

*Leaflet apex.*—Acuminate.

*Leaflet base.*—Obtuse.

*Leaflet margin.*—Serrate.

*Leaflet texture, upper and lower surfaces.*—Smooth, glabrous.

*Leaflet luster, upper and lower surfaces.*—Glossy.

*Leaflet venation pattern.*—Pinnate.

*Leaflet color.*—Developing leaflets, upper and lower surfaces: Close to 144B. Fully expanded leaflets, upper surface: Close to 141B; venation, close to 138C. Fully expanded leaflets, lower surface: Close to 141C; venation, close to 145C.

*Leaf petioles.*—Length: About 2 cm. Diameter: About 2 mm. Texture, upper and lower surfaces: Smooth, glabrous. Color, upper and lower surfaces: Close to 146B.

Flower description:

*Flower type and habit.*—Rotate rounded flowers arranged singly; flowers face mostly upright or outwardly; freely flowering with plants developing about 120 flowers during the flowering period.

*Natural flowering season.*—Plants flower continuously in the landscape during the summer in Grand Haven, Mich.; during this period flowering is continuous; flowers persistent.

*Fragrance.*—Moderately fragrant; sweet, pleasant.

*Flower buds.*—Height: About 2.5 cm. Diameter: About 1 cm. Shape: Ovoid. Texture: Rugose, glabrous. Color: Close to 47B.

*Flower diameter.*—About 6.5 cm.

*Flower depth.*—About 3 cm.

*Petals.*—Quantity per flower: About 24 in several whorls. Length: About 3 cm. Width: About 2.6 cm. Shape: Obovate. Apex: Obtuse. Base: Attenuate. Margin: Entire. Texture, upper and lower surfaces: Smooth, glabrous. Aspect: Initially upright becoming more flat, margins incurved with development; undulate. Color: Developing petals, upper and lower surfaces: Close to 53D; towards the base, close to 2A. Fully expanded petals, upper and lower surfaces: Close to 54A; towards the base, close to 54A and 2A; upper surface with small basal spot, close to 159B and 1B in color; with development, color becoming closer to 68B to 68C and towards the base, close to 2C.

*Sepals.*—Quantity per flower: Five. Length: About 2 cm. Width: About 6 mm. Shape: Subulate. Apex: Acuminate. Base: Cuneate. Margin: Entire; ciliate. Texture, upper and lower surfaces: Smooth, glabrous. Color: Developing and fully expanded sepals, upper surface: Close to 144A. Developing and fully expanded sepals, lower surface: Close to 144C.

*Peduncles*.—Length: About 3.5 cm. Diameter: About 2 mm. Orientation: Erect to about 10° from vertical. Strength: Strong. Color: Close to 144A.

*Reproductive organs*.—Stamens: Quantity per flower: Numerous, about 84. Anther shape: Oblong. Anther length: About 1 mm. Anther color: Close to 53A. Pollen amount: Moderate. Pollen color: Close to 4D. Pistils: Quantity per flower: About 31. Pistil length: About 1.5 cm. Stigma shape: Round. Stigma color: Close to 22B. Style length: About 4 mm. Style color: Close to 50B. Ovary color: Close to 144A.

*Fruits*.—Diameter: About 1 cm to 1.5 cm. Shape: Globular. Color: Close to 144A; with frost, color becoming closer to 200A.

*Seeds*.—Diameter: About 4 mm to 5 mm. Shape: Roughly tear-shaped. Color: Close to 160B.

Pathogen & pest resistance: Plants of the new Rose have been observed to be resistant to Black Spot (*Diplocarpon rosae*). Plants of the new Rose have not been observed to be resistant to pests and other pathogens common to Rose plants.

Garden performance: Plants of the new Rose have been observed have good garden performance and to tolerate rain, wind and temperatures ranging from about −25° C. to about 30° C.

It is claimed:

1. A new and distinct Rose plant named 'Hornimrod' as illustrated and described.

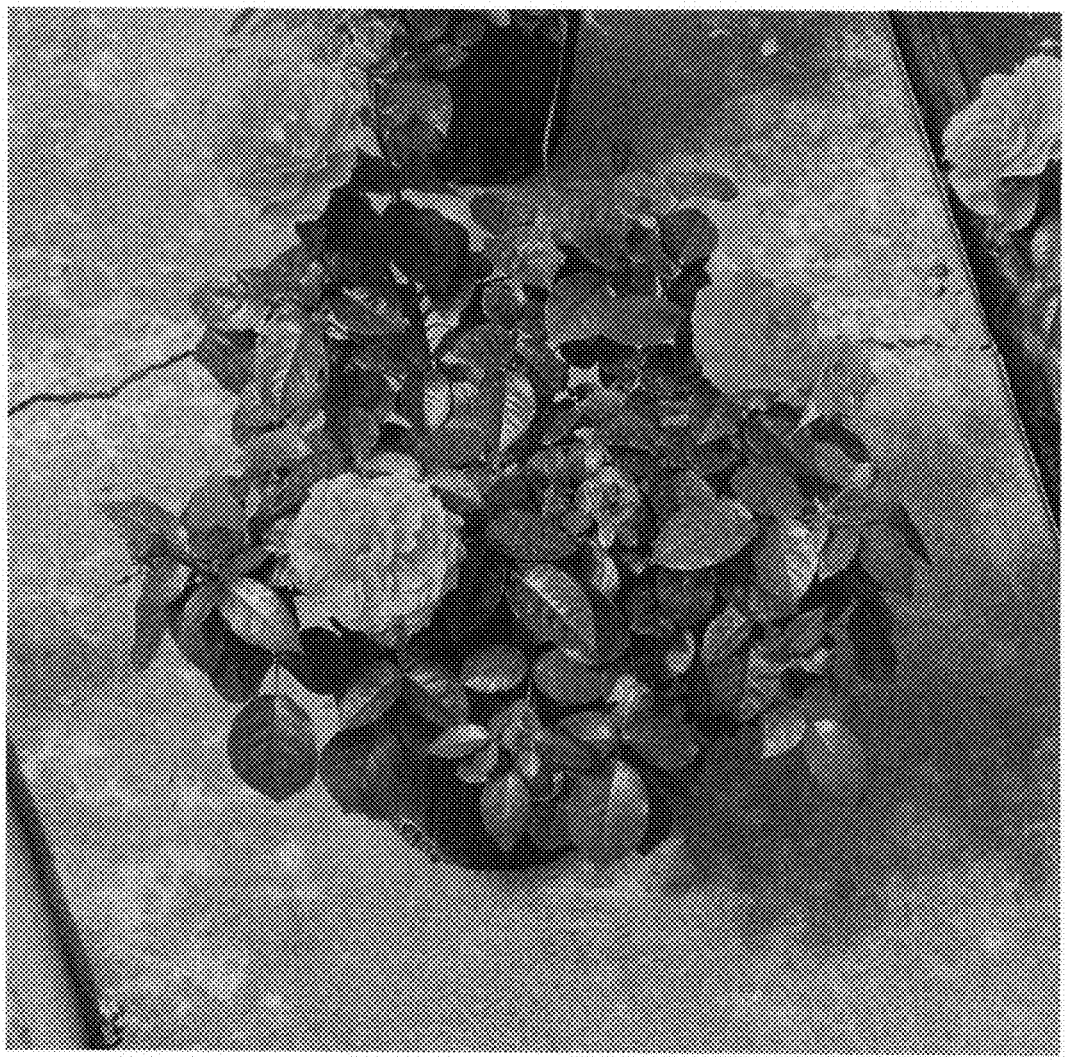

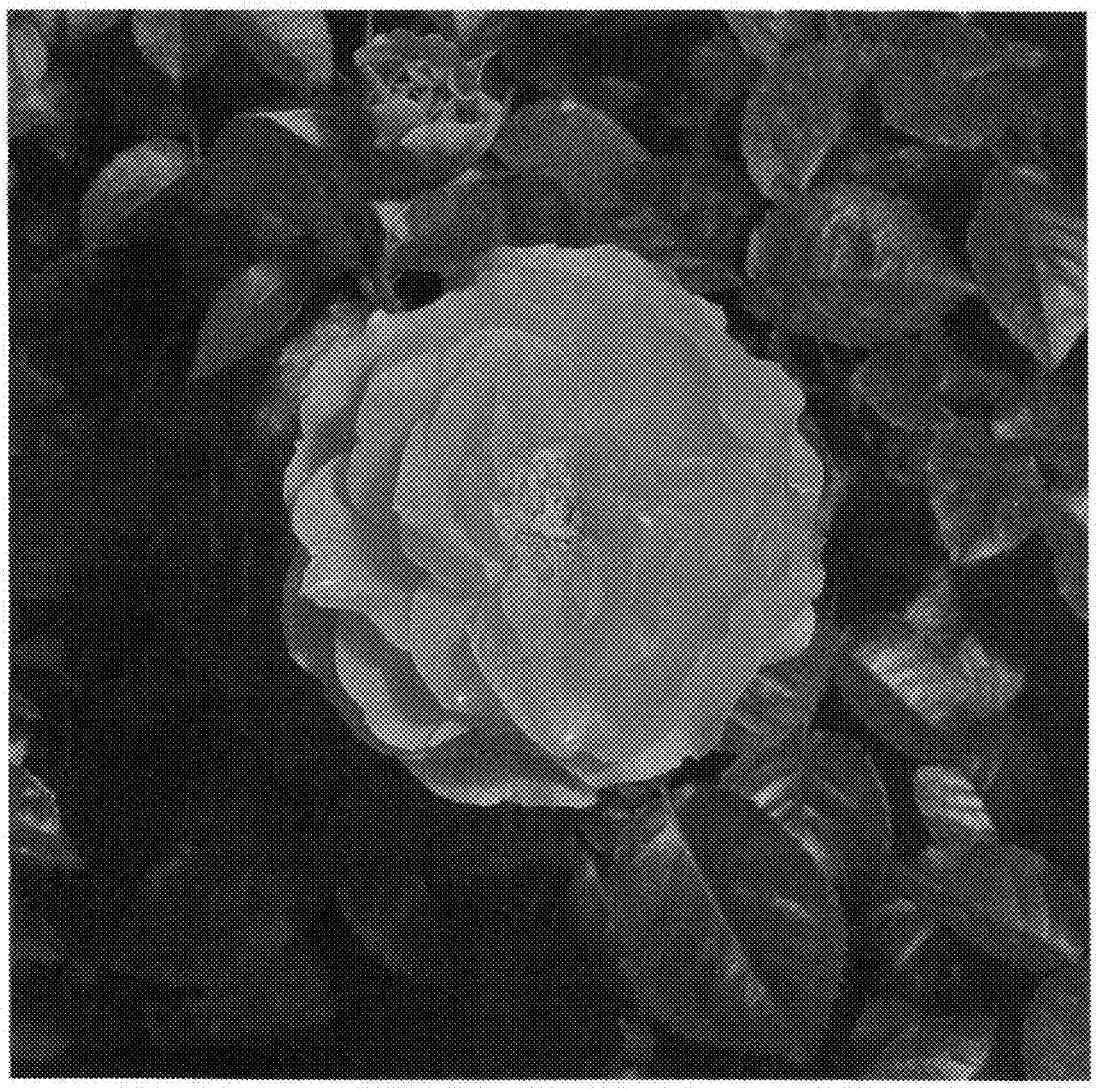

* * * * *